(12) United States Patent
Perrins et al.

(10) Patent No.: US 6,215,847 B1
(45) Date of Patent: Apr. 10, 2001

(54) PRODUCT IRRADIATOR

(75) Inventors: Rob Perrins, Kanata; Dave Gerwing, Greely, both of (CA)

(73) Assignee: MDS Nordion Inc., Kanata (CA)

( * ) Notice: Subject to any disclaimer, the term of this patent is extended or adjusted under 35 U.S.C. 154(b) by 0 days.

(21) Appl. No.: 09/153,669

(22) Filed: Sep. 15, 1998

(51) Int. Cl.$^7$ .......................... G01N 21/00; G01N 23/00; G21K 5/00
(52) U.S. Cl. ......................................... 378/69; 250/453.11
(58) Field of Search .................... 378/68, 69, 64; 250/453.11, 454.11

(56) References Cited

U.S. PATENT DOCUMENTS

| | | | |
|---|---|---|---|
| 3,564,241 | 2/1971 | Ludwig | 378/69 |
| 3,673,409 | 6/1972 | Green | 378/69 |
| 3,676,675 | 7/1972 | Ransohoff et al. | 378/69 |
| 4,018,348 | 4/1977 | Bosshard | 414/287 |
| 4,066,907 | 1/1978 | Tetzlaff | 378/69 |
| 4,151,419 * | 4/1979 | Morris et al. | 378/69 |
| 4,481,652 | 11/1984 | Ransohoff | 378/69 |
| 4,760,264 | 7/1988 | Barrett | 250/453.11 |
| 4,788,701 | 11/1988 | Barrett | 378/69 |
| 4,852,138 | 7/1989 | Bergeret et al. | 378/69 |
| 4,866,281 | 9/1989 | Bosshard | 378/69 |
| 5,001,352 | 3/1991 | Tetzlaff | 378/69 |
| 5,396,074 | 3/1995 | Peck et al. | 250/453.11 |
| 5,400,382 | 3/1995 | Welt et al. | 378/69 |

OTHER PUBLICATIONS

Nordion International Inc., Tote Irradiator, JS–9500 & JS–9600.
Nordion International Inc., High Performance Tote Irradiator, JS–10000.
MDS Nordion, Gamma Processing.
Nordion International Inc., Brinston and Norton, Colbalt 60: The Heart of Gamma Radiation Sterilization.
Nordion International Inc., JS–9500/9600 Tote, Performance Data Sheet 9501.

* cited by examiner

Primary Examiner—David V. Bruce
Assistant Examiner—Drew A. Dunn
(74) Attorney, Agent, or Firm—Haynes and Boone LLP

(57) ABSTRACT

The present invention is directed to a product irradiator comprising a loading-unloading area and an irradiation chamber, a continuous track having a level-changing portion, wherein the continuous track enters and exits the irradiation chamber from the loading-unloading area. The continuous track is comprised of at least one rail and of at least two levels to about 8 levels. An irradiation source, for example cobalt 60, and which is preferably horizontal in orientation, is located within the irradiation chamber. The product irradiator comprises a substantially horizontal carrier, which is engaged to the continuous track, and at least one drive mechanism capable of moving the carrier along the continuous track.

39 Claims, 13 Drawing Sheets

PRODUCT IRRADIATOR

The present invention relates to a multipurpose product irradiator. More specifically this invention relates to an irradiator useful in irradiating medical, food and other products or articles.

BACKGROUND OF THE INVENTION

Irradiation systems are used for irradiating medical devices, foodstuffs, food utensils, as well as other goods such as cosmetics, waste products and the like. Typically high energy ionizing radiation is used as the radiation source, for example gamma radiation, X-ray, electron beam, or the like. The source, in the case of a radioisotope, is typically maintained beneath the irradiation chamber within a pool when not in use, and raised into position as required. Articles of interest are placed upon pallets, or loaded into unique carrier trays, and these pallets or carriers are conveyed past the radiation source in order to expose the contents therein.

It is well known within the art, that even exposure of the article to the source will provide a more optimum irradiation. In this regard, the dose-uniformity ratio (DUR), which is the ratio between the maximum and minimum dose that a product receives, is used as a measure for exposure uniformity. In order to optimize the DUR, several conveyor-track assembly, and their relationship with radiation source locations have been considered.

Many prior art irradiators utilize conveyors in order to move a product laden carrier past an radiation source, for example U.S. Pat. Nos. 5,396,074, 5,001,352, 4,866,281, 4,852,138, 4,561,358, 4,481,652, 3,676,675 or U.S. Pat. No. 3,564,241. These irradiators utilize a source-overlapping-product configuration, and operate with a low efficiency of source utilization. Furthermore, these systems necessitate the use of many moving mechanical parts within the irradiation chamber, yet the environment within the irradiation chamber is hard on many plastics and metals. Such designs are therefore prone to repeated failures that require full shutdown of the irradiator for repair. Similarly, other transport systems, (U.S. Pat. Nos. 4,066,907, 4,018,348) use turntables coupled with conveyor systems to expose a product to a source. These systems also comprises many moving parts within the radiation chamber, and necessitate substantial product handling within the irradiation chamber. Furthermore, all of the above irradiators require extensive unpackaging and repackaging of the product from a pallet to the carrier, and following radiation treatment back, onto the pallet for shipping.

Other irradiators have adopted an alternate transport system with which to move a product past a source. In U.S. Pat. No. 5,396,074 there is disclosed a facility for irradiating foods and medical devices using an electron beam as the radiation source. An overhead transport conveyor is used to suspend article carriers to permit their movement around a track and to bring these carriers in front of the radiation source. The suspended article carriers are capable of rotating upon their vertical axes which permits radiation of two sides of a product disposed within the article carrier. This design permits exposure of both sides of the article carrier to the radiation source. However, radiation by electron beam may result in a poor depth of penetration in medium to high density products (i.e. over about 0.4 g/cc), and extensive repackaging is required in order for such products to be treated effectively with a low resulting DUR. This type of irradiator therefore has a limited use. A similar conveying system is found in U.S. Pat. No. 4,481,652 and U.S. Pat. No. 3,673,409, with carriers suspended from a monorail-type track. This system uses cam-catch members that are powered in order to push the product carriers through the labyrinth path before the gamma radiation source.

U.S. Pat. No. 5,400,382 is directed to irradiating products, located on pallets moved on shuttle cars, with gamma rays. The shuttle cars move the pallets into the region of the gamma source, on a series of parallel tracks, and the pallets are transferred from track to track so that each side of the object being irradiated is exposed. Again, with such a design there are many moving parts located within the irradiation chamber thereby minimizing access for maintenance and repair. Furthermore, these irradiators use a source-overlapping-product configuration which results in a low efficiency of radiation utilization.

Several irradiator designs do not require the introduction of the source into the irradiation chamber, rather the product is lowered into the pool surrounding the source. For example, U.S. Pat. No. 3,676,675 is directed to a subterranean production irradiator with a product conveyor system comprising an endless chain and sprockets arranged to permit movement of specialized product carriers past an radiation source. The product carriers are hung from the chain, and pass over and under the source in a sinusoidal path. A similar approach is disclosed in U.S. Pat. No. 4,760,264; 4,908,221; 5,008,550 which incorporates a water-tight duct system through which carriers are passed. The conveyor system comprises a continuous chain in order to move the product through the duct system. In all of these designs, the speed of the conveyor effects all carriers attached to the conveyor, any variation in speed affects all product carriers at the same time throughout the ductwork. Any mechanical problem localized within the subterranean irradiation chamber is also very difficult to repair, and this is complicated by the fact that the source can not be easily removed from the irradiation chamber resulting in time consuming maintenance or repair procedures. Due to the types of carriers employed, extensive product handling in order to load and unload the carriers from, and to, a pallet is required.

U.S. Pat. No. 4,561,358 is directed to an apparatus for conveying elongated articles through an radiation beam. The conveying means comprises two overhead tracks, and a guide that associates with, but is located below the carrier to direct the orientation of the article and permit both sides of the articles to be exposed to the radiation source. U.S. Pat. No. 3,564,241 is directed to an irradiation apparatus comprising a continuous horizontal track to form a single path around a radiation source.

U.S. Pat. No. 4,066,907 discloses the use of a turntable with several levels that circumscribes a vertically placed source. This configuration permits the partial exposure of the top and bottom of the product to the source. The product is moved onto the turntable by a goods handling appliance, such as a fork lift coupled with a telescopic table. The same goods handler is also used to transfer product between levels of the turntable in order to permit exposure of the sides and a portion of the top and bottom of the product to the source. All of this material handling takes place within the irradiation chamber. Due to the harsh environment within the irradiation chamber, routine maintenance requires shutdown of the irradiator. The carriers used within each irradiators also require extensive product handling and repackaging in order to load and unload the carriers. These irradiators also employ a source-overlapping-product configuration which results in a low efficiency of radiation utilization.

Several problems exist with most prior art product irradiators. Many designs require considerable carrier handling within the irradiation chamber either to complete a pass around the source, or to effect a change in the level of turntable or conveyor. Furthermore, several designs require extensive carrier loading and unloading before an after exposure to the source, due to the use of specialized carrier trays used for product radiation. This is especially true if the product is orientation-sensitive and must be loaded in a specific manner prior to treatment. Furthermore, carriers of the prior art do not easily permit variable product heights to be easily loaded or continuously passed around the source. In general, product packaging limitations result in limited flexibility of irradiator use.

As a result of the required carrier handling devices and associated mechanism, as well as track or conveyor configurations, or carrier designs, there is much support or structure between the source and product within many prior art irradiators. This structure attenuates the radiation emitted from the source and reduces the efficiency of radiation utilization within the irradiator. Furthermore, many prior art irradiators adopt a source-overlapping-product configuration and this further results in an a lower efficiency of radiation utilization.

The environment within the irradiation chamber is also harsh on components that are subject to repeated radiation exposure including the product carriers, transfer mechanisms, pulleys, bearings and track assemblies. For example, gamma radiation, through cross linking, degrades carbon based, and related materials, including lubricants, plastics, non-metallic seals and the like. Furthermore, when the surrounding air is irradiated, ozone is produced which is a strong oxidant that corrodes ferric metals. Therefor, any suitable product irradiator design should consider minimizing the number of moving parts within the irradiation chamber, as well as permitting the easy removal of components repeatedly exposed to radiation in order to minimize downtime of the irradiator.

The product irradiator of the present invention sets out to overcome the deficiencies identified within the art, and ensures an optional dose uniformity ratio (DUR). In addition, the number of moving parts exposed to the irradiation chamber environment has been reduced in order to minimize effects of radiation and ozone on the components. Furthermore, most of the moving parts spend a substantial portion of time outside the irradiation chamber, which extend their use and reduces maintenance, and provides for easy access for repair and replacement. The design of the present invention also permits easy removal of components from the irradiation chamber for repair thereby minimizing down time of the product irradiator.

The carriers of the product irradiator of the present invention are designed to minimize or eliminate product repackaging, and ensure that palleted goods can be placed onto appropriately sized carriers and, following treatment, can be easily repalleted. A result of easy carrier loading and unloading results in greater product throughput. The product irradiator of the present invention also incorporates a carrier that can be used with orientation-sensitive goods, and readily accommodates goods that vary in height.

Another problem associated with prior art irradiators, is that the carriers can not accommodate wide variations in product size since the carriers used are of a fixed dimension, and the track, or conveyor, assemblies are fixed at preset distances from the source. Typically, the DUR for a product is specified and the packing of product within the carrier is altered to achieve the desired DUR specification for a given pass. Often such packing results in low packing efficiencies within the carrier, which translates into reduced product throughput. Furthermore, non-optimal packing also leads to low utilization efficiencies of the source. The design of the present invention provides for an adjustable carrier height with respect to the track and this feature accommodates a wide range of product dimension, while maintaining the DUR within required specified ranges. This means that, instead of manually arranging product loading to meet the required specified DUR for a given product class, the irradiator design of the present invention allows the operator to automatically achieve the desired DUR while also maximizing throughput.

The irradiator of the present invention also provides for greatly reduced product support structure between the source and product thereby reducing attenuation and increasing the efficiency of source utilization. Furthermore, the irradiator may be used in either a product-overlapping-source, or a source-overlapping-product configuration as required.

The product irradiator of the present invention also involves the use of a continuous track with level-changing portion which provides a novel path for a product laden tray to circumscribe a source through a variety of heights, and from a variety of directions. Such a path results in an optimal DUR.

SUMMARY OF THE INVENTION

The present invention relates to a multipurpose product irradiator. More specifically this invention relates to an irradiator useful in irradiating medical, food and other products or articles.

According to the present invention there is provided a product irradiator comprising:

i) a loading-unloading area and an irradiation chamber;
  ii) a continuous track that enters and exits said irradiation chamber from said loading-unloading area, said continuous track having a level-changing portion, said continuous track comprised of at least one rail and at least two levels;
  iii) an radiation source, located with said irradiation chamber;
  iv) a carrier, attached along one side to a wheel assembly, said wheel assembly engaged to said at least one rail, said carrier extending substantially horizontally from said continuous track; and
  v) at least one drive mechanism capable of moving said carrier along said continuous track.

This invention is also directed to a product irradiator as defined above wherein said radiation source is either cobalt 60 or cesium 137.

Also included within the present invention is a product irradiator as defined above wherein said continuous track comprises up to eight levels of track within the irradiation chamber, preferably comprising either two, four, six or eight levels of track within the irradiation chamber. Furthermore, the track may be comprised of two rails, and these rails may be offset within respect to each other. The continuous track may have an elongated helical conformation within the irradiation chamber.

This invention also embraces a product irradiator above wherein said radiation source is centrally positioned within an elongated helical portion of continuous track, lying in a substantially horizontal plane within said irradiation chamber. Furthermore, this invention relates to a product irradiator as defined above wherein said radiation source is positioned with an equivalent number of said levels of continuous track lying above an imaginary horizontal plane extending from said radiation source, as levels of continuous track that lie below said imaginary horizontal plane extending from said radiation source.

This invention is directed to a product irradiator, defined above, further comprising a product re-orienting mechanism. This invention also includes a product irradiator comprising at least two carriers, wherein said product re-orienting mechanism is a pusher capable of transferring said product from a first carrier to a second carrier. The product irradiator of present invention may also adopt a product-overlapping-source configuration.

This invention relates to a product irradiator as defined above wherein said radiation source is stored below the irradiation chamber, and is brought into a substantially horizontal position within said irradiation chamber using a source rack hoist and guide assembly.

This invention also embraces a product irradiator, defined above, wherein said irradiation chamber is temperature controlled and ranges from about −25° C. to about 25° C.

The product irradiator of the present invention may also comprise a multipiece roof plug, permitting access to the irradiation chamber and a source storage area.

This invention also pertains to the product irradiator as defined above wherein at least one, of said at least one drive mechanism, comprises a chain drive with a plurality of outwardly extending pins, each of said plurality of outwardly extending pins capable of engaging with a dog attached to said carrier and pivotally biased in the direction of the chain drive, so that when said dog is engaged with one of said plurality of outwardly extending pins, said carrier is moved along said track by said chain drive. The product irradiator, as defined above, may also comprise a stop link capable of disengaging said dog from one of said outwardly extending pins, thereby permitting said carrier to stop along said track, and allowing said carrier to travel along said continuous track at a different speed.

This invention also embraces the product irradiator as defined above, wherein the height of said carrier, with respect to said continuous track, can be altered by a height adjust mechanism. This mechanism includes a screw mechanism, a ramp mechanism, a piston-driven mechanism, a ratchet mechanism, or a combination thereof.

This invention is directed to the product irradiator, defined above, characterized with a dose-uniformity-ratio of up to about 3.5 for a product having a density of about 0.01 to about 0.9 g/cc, and said product between from about 6 to 36 inches in height.

This invention also relates to a product irradiator comprising:
i) a temperature controlled building, within which is located a loading-unloading area, a maze, an irradiation chamber, and a radiation source storage area, said building comprised of concrete, lead, or both concrete, and lead, wherein the temperature of said loading-unloading area, maze, and irradiation chamber is from about −25° C. to about 25° C.; said building further comprising a multipiece roof plug permitting access to said irradiation chamber and radiation source storage area;
ii) a continuous track extending from said loading-unloading area through said maze and into said irradiation chamber, said continuous track having a level-changing portion, and comprised of at least one rail, said continuous track comprising either two, four, six or eight levels;
iii) at least two carriers, each carrier comprising a slave tray and a wheel assembly, said wheel assembly engaged with said at least one rail and pivotally attached along one side of each carrier, each carrier extending substantially horizontally from said continuous track toward said radiation source;
iv) at least one drive mechanism capable of moving each of said at least two carriers along said continuous track from said loading-unloading area, through said maze, into said irradiation chamber around said helical portion of said continuous track, thereby changing horizontal and vertical position of said carrier with respect to said radiation source within said irradiation chamber, exiting said irradiation chamber, and travelling through said maze to said loading-unloading area;
v) a pusher capable of transferring a product located upon said slave tray from a first carrier to a second carrier;
vi) an radiation source stored below said irradiation chamber within said source storage area, said source brought into a substantially horizontal position within said irradiation chamber using a source rack hoist and guide assembly, when positioned within said irradiation chamber said radiation source is located centrally, on a horizontal plane, within said elongated helical portion of said track, and positioned with an equivalent number of levels of continuous track lying above an imaginary horizontal plane extending from said radiation source, as levels of continuous track that lie below said imaginary horizontal plane extending from said radiation source; said radiation source adopting a product-overlapping-source configuration with respect to said product, said radiation source selected from either cobalt 60 and cesium 137.

The product irradiator of the present invention overcomes many of the problems identified within the prior art. The number of moving parts exposed to the irradiation chamber environment is reduced in order to minimize effects of irradiation and ozone on the components. Furthermore, the duration of exposure of such moving pats is reduced within the irradiation chamber. The design of the present invention also permits easy removal of components from the irradiation chamber for repair thereby minimizing down time of the product irradiator. The carriers of the product irradiator of the present invention are designed in order to minimize or eliminate product repackaging, and ensures that palleted goods can be placed into appropriately sized carriers and, following treatment, can be easily repalleted. Furthermore, the carrier of the present invention can be used with orientation-sensitive goods, or goods that vary in height. These features result in a greater product throughput, and flexibility in the use of the irradiator, permitting a variety of products to be treated.

The product irradiator of the present invention provides for adjustment in the height of the carrier and allows products of varying dimensions to be easily loaded and transported past the source while maintaining product specific DURs and maximizing throughput. For a horizontal source rack, this flexibility is provided by adjusting the vertical (height) of the carrier. For a vertical source rack, this flexibility is provided by adjusting the horizontal (width) dimension.

This invention is also directed to a product irradiator comprising: a loading-unloading area and an irradiation chamber; a conveying means; a radiation source located within said irradiation chamber; a carrier; and, at least one drive mechanism capable of moving said carrier along said conveying means, wherein at least one dimension of said carrier is variable. The carrier of the product irradiator as defined immediately above may comprise a wheel assembly that is adjustable in said at least one dimension. Furthermore, the product irradiator as defined immediately above may comprise a source that is oriented horizontally within said irradiation chamber, and said at least one dimension is the height. Similarly, the product irradiator may comprise a source that is oriented vertically within said irradiation chamber, and said at least one dimension is the width.

This invention also embraces a product irradiator as defined in the preceding paragraph wherein said conveying means is selected from an overhead track, a under-carrier track, or a combination thereof. The conveying means may also comprise a conveyor. Furthermore, this invention includes a product irradiator as defined in the preceding paragraph wherein said conveying means comprises more than one level.

The irradiator of the present invention also provides for greatly reduced product support structure between the source and product which results in lower levels of attenuation. The product irradiator of the present invention employs the use of a continuous track, which can adopt a helical conformation within the irradiation chamber. This track design provides a novel path for a product laden carrier to circumscribe a source through a variety of heights, and from a variety of directions, and reduces the requirement for extensive mechanical carrier handling within the irradiation chamber. Such a path results in an optimal DUR within the treated product.

BRIEF DESCRIPTION OF THE DRAWINGS

These and other features of the invention will become more apparent from the following description in which reference is made to the appended drawings wherein:

FIG. 1 shows in top view, as aspect of an embodiment of the product irradiator of the present invention.

FIG. 4(A) shows a top view, FIG. 4(B) shows a side view. In FIG. 4(B), each circular end of the track comprises a helical portion (level changing portion), however, the helical portion may be positioned elsewhere, for example at one circular end of track.

FIG. 5 shows, in side and top view, an aspect of an embodiment of the product irradiator of present invention and indicates a carrier.

DESCRIPTION OF PREFERRED EMBODIMENT

Figure 1A:
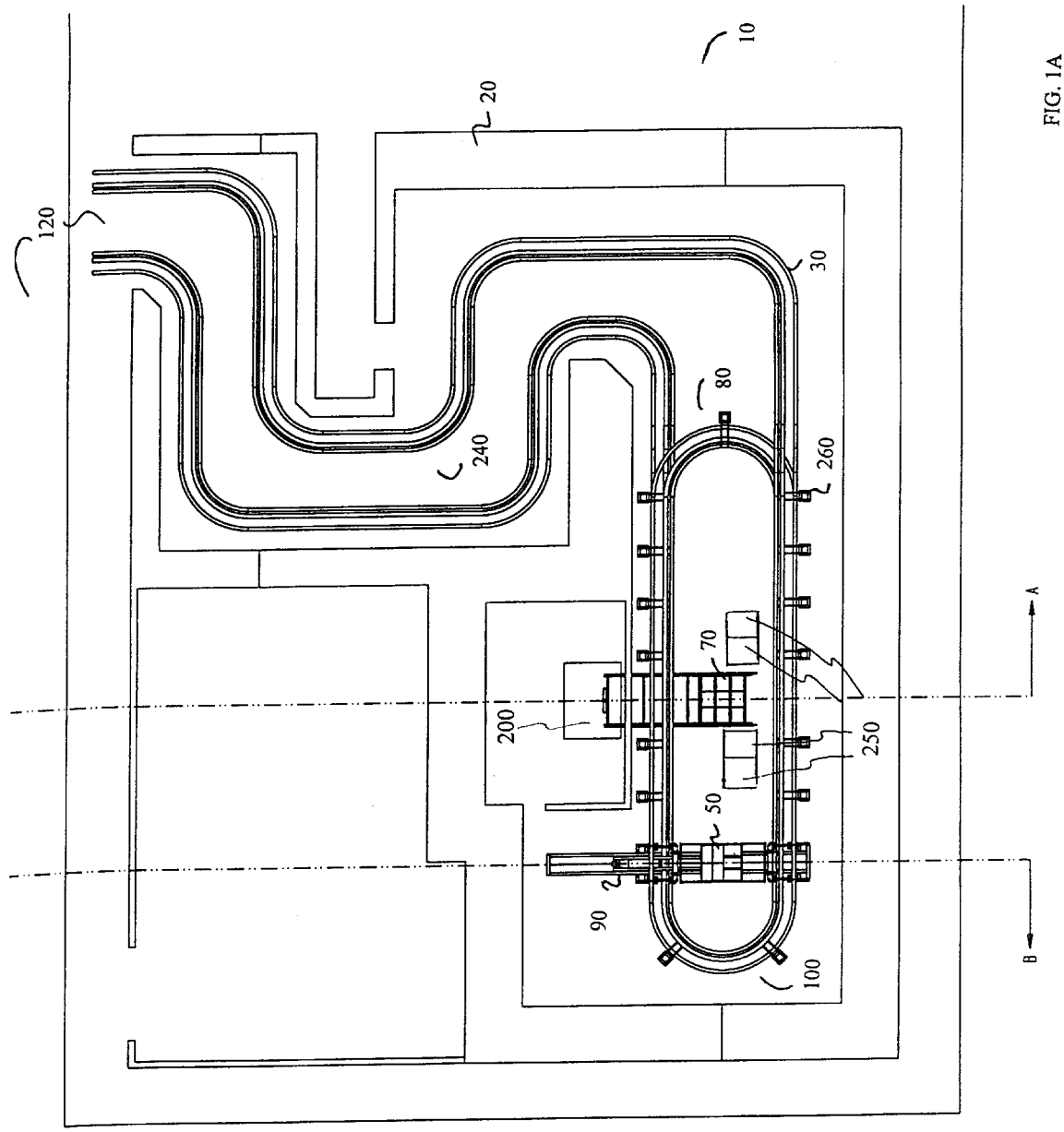
FIG. 1(A) shows a top view.

The present invention relates to a multipurpose product irradiator. More specifically this invention relates to an irradiator useful in irradiating medical, food and other products or articles.

Having regard to the figures, the product irradiator of the present invention, generally indicated as (10) (FIG. 1A) is situated within a suitable building (20) typically made from concrete, lead or other material that helps reduce radiation levels on the outside of the structure. The environment within the building (20) may be temperature controlled and can vary from about −25° C. to about 25° C. in order to match warehouse temperature. The roof of the building comprises a multipiece roof plug (250), permitting access to the irradiation chamber (110), or source (70), or elsewhere for maintenance as required. Below the irradiation chamber is a pool (200) that houses the source rack (70), when the source is not in use.

Figure 1B:
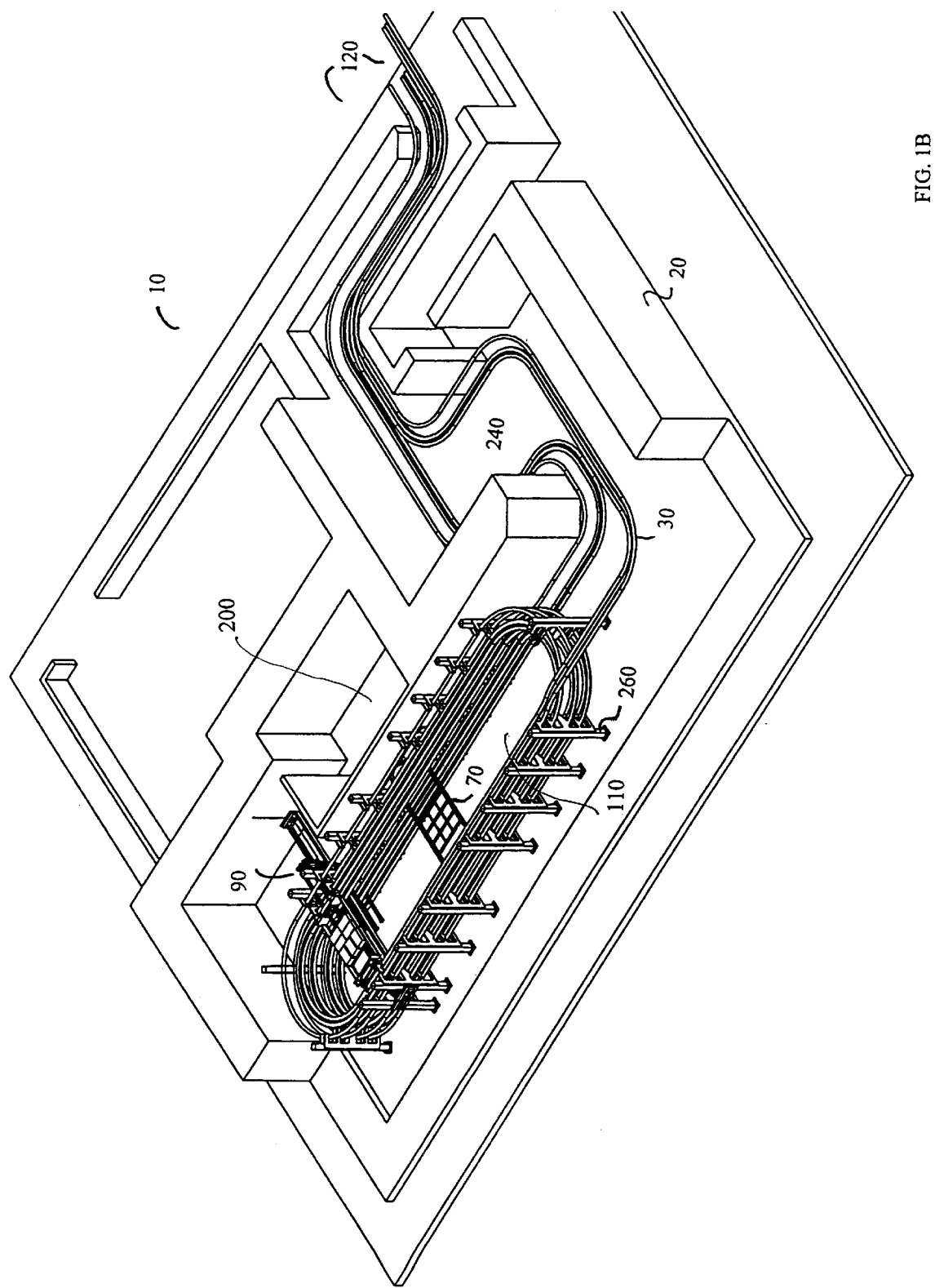
FIG. 1(B) shows a 3-D view.
Figure 1C:
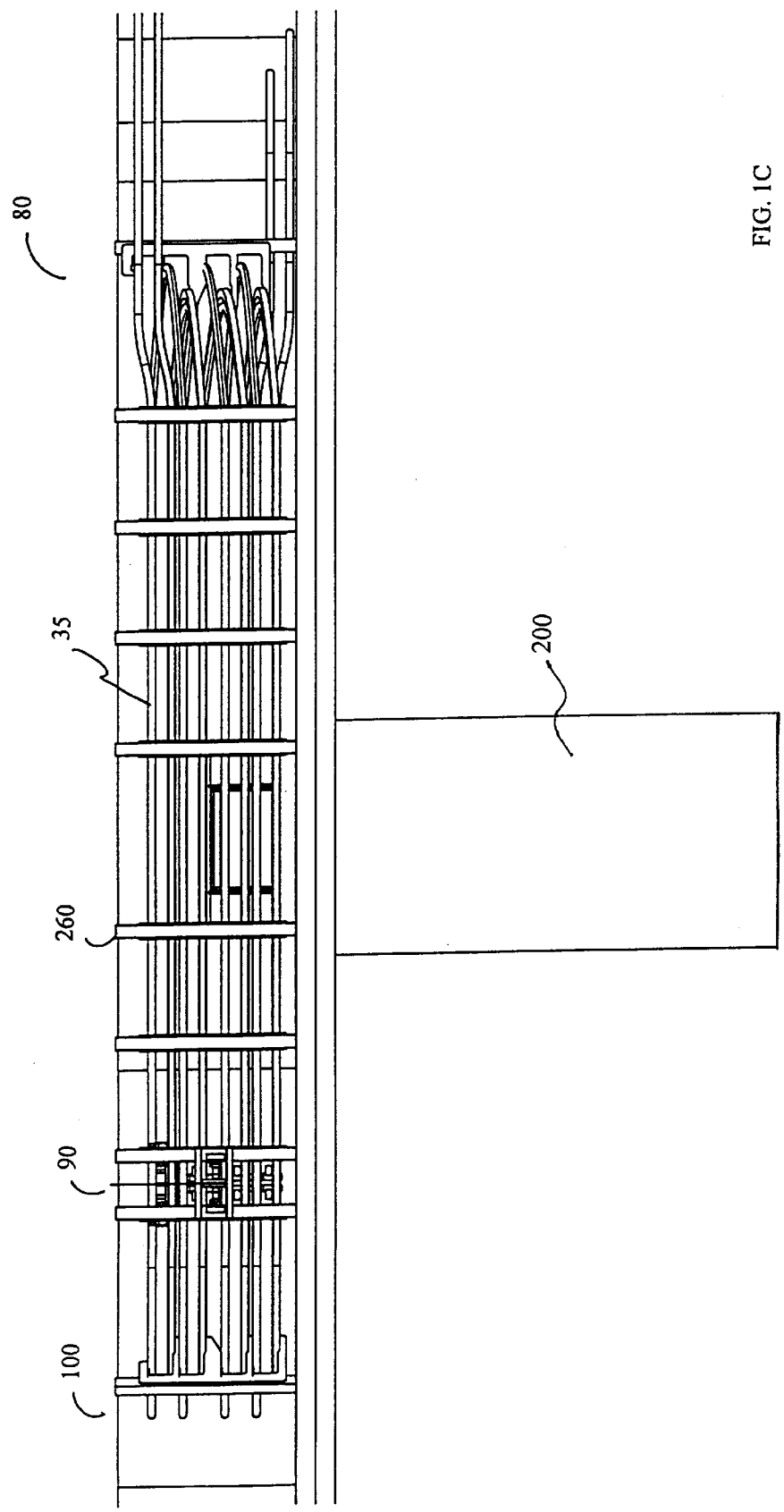
FIG. 1(C) shows a side view of a product irradiator.
Figure 2:
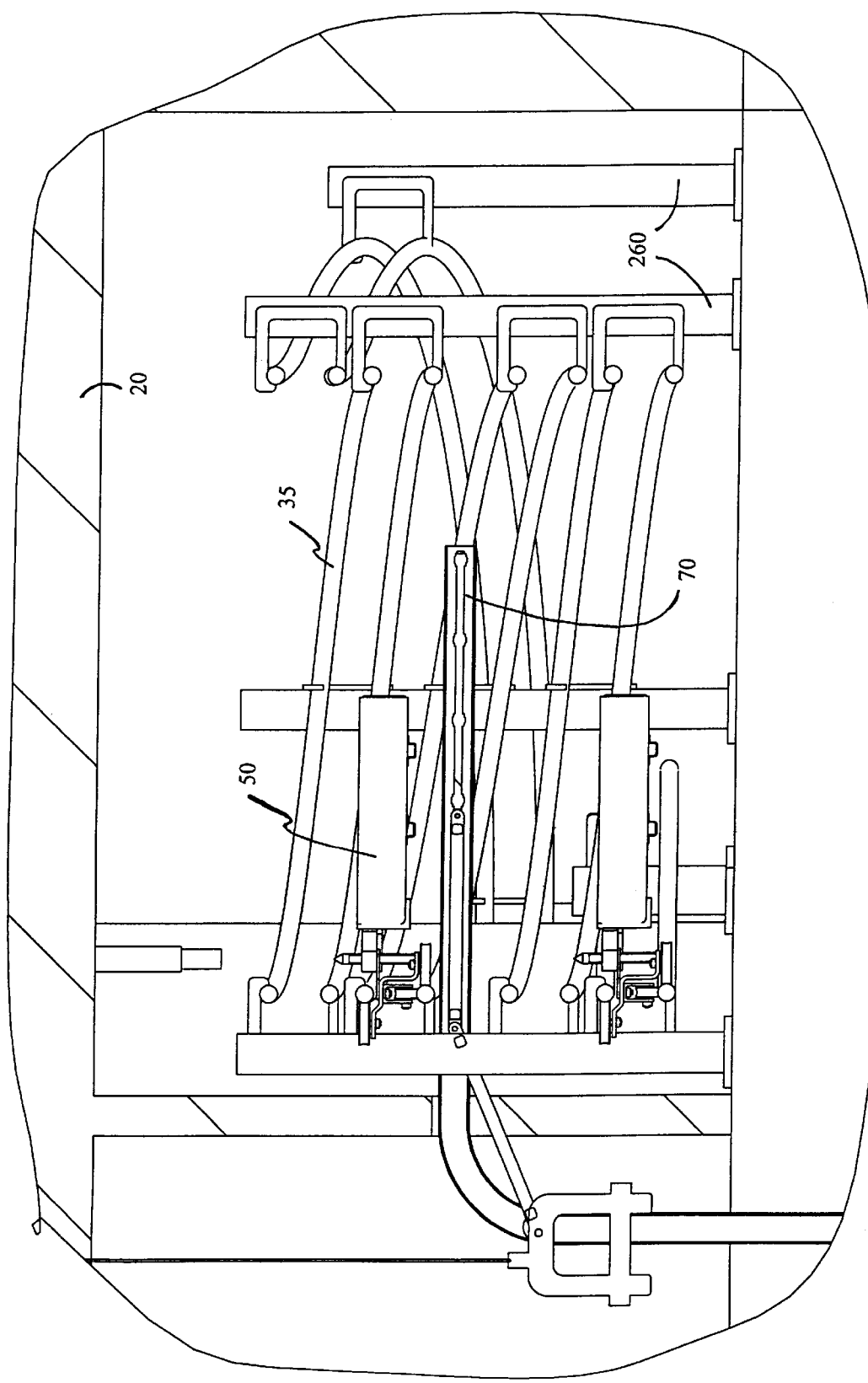
FIG. 2 shows in side view, an aspect of an embodiment of the product irradiator of present invention comprising the change in height of the helical track within the irradiation chamber.
Figure 4:
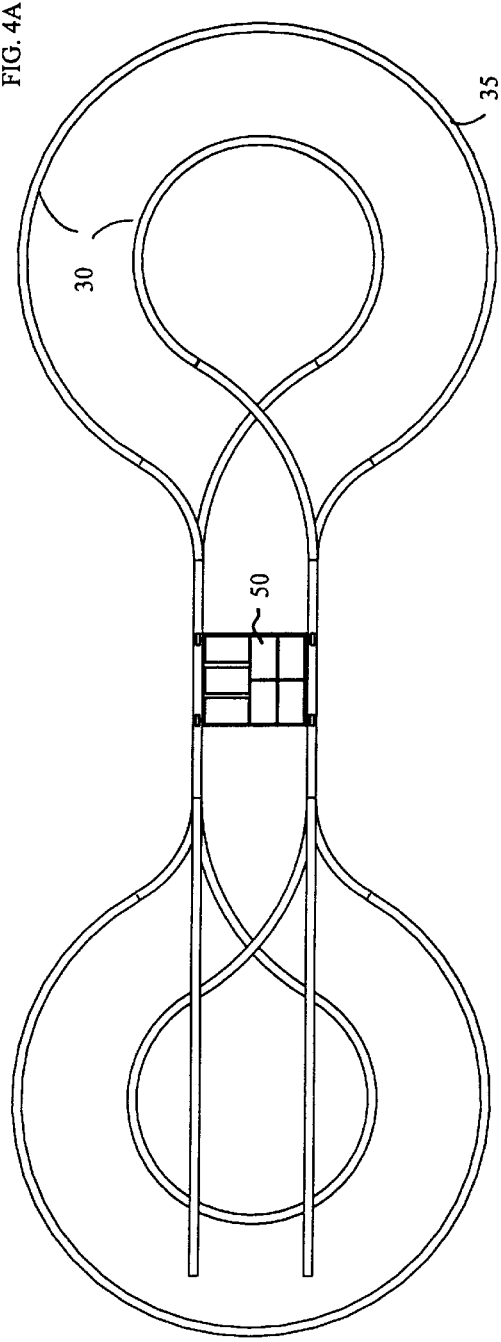
FIG. 4 shows, in top view, an aspect of an embodiment of the product irradiator of the present invention and indicates a bar-bell type track layout.
Figure 4:
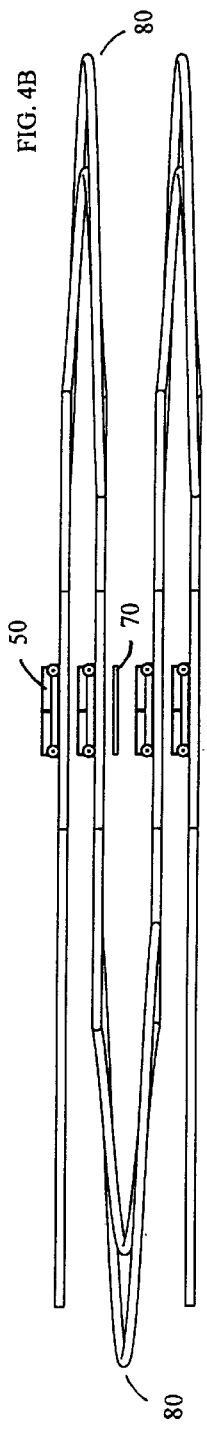

Within the building is a track assembly (30) composed of at least one rail (35; FIG. 2). The track is attached to the building through appropriate supports (260). The track extends from a loading-unloading area which is not shown, but is generally indicated as 120 in FIGS. 1A and 1B, through a maze, generally indicated as 240, and into the irradiation chamber (110) where it adopts a desired conformation, for example an elongated helical track, which comprises a plurality of levels. The maze (240) may comprise more labyrinth-like corridors, as required, to effectively shield emissions from the irradiation chamber. The track also exits the irradiation chamber, returning back to the loading-unloading area (120) where it is continuous with the track leading back into the maze. The continuous nature of the track within the loading-unloading area is not shown in FIGS. 1A, 1B or 1C. This helical path permits the travel of a carrier (50) engaged with the track through a wheel assembly (140) to either circumscribe a centrally positioned source (70) as shown in FIGS. 1A, 1B or 1C, or to traverse a source as shown in FIG. 4B. The helical path of the present invention alters the carriers elevation as the carrier travels around the helical portion of the track. In this embodiment (FIG. 1), the helical portion of the track comprises a level-changing portion.

The track of the present invention is continuous from the loading-unloading area through to the irradiation chamber. However, it is to be understood that even though a continuous track is desired, slight variations in this design may exist without departing from the spirit or scope of this invention. For example, it may be desired for a portion of the track to provide access or departure points within the continuous track, and such points may be provided through the movement of a section of track via suitable means. Similarly, a level-changing portion of track may also be adjusted or engaged via the movement of a section of track via suitable means. In this regard, the track of the present invention is continuous in nature, even though several sections of track may be able to reversibly disengage with the track. It is to be understood that the level-changing portion of track may be located along a linear portion of track, or at a circular (i.e. helical portion) as desired. Furthermore, the circular end portion, level changing portion, or both portions of track, may physically reside outside the irradiation chamber should this be desired. Similarly, any product re-orienting mechanisms may also be placed outside of the irradiation chamber in order to reduce the number of moving or mechanical parts within the irradiation chamber.

The product to be treated is introduced into the irradiator from a pallet supply within the loading-unloading area (120). The loading and unloading of carriers may take place manually or via robotics. The carriers are configured to optimize packaging efficiency and are dimensioned to match the pallet foot print in order to accommodate layers of a pre-palleted product and ensure that carriers can be easily loaded and unloaded as needed. Following treatment within the irradiator, the product trays are easily re-palleted and wrapped as required by the customer. In doing so, the product throughput within the irradiator of the present invention is greatly enhanced over that of prior art irradiators. It is also to be understood that the carriers of the present invention may be insulated in order to ensure that the product contained therein is maintained at a desired temperature. Such insulated carriers may also be used should the building housing the irradiator not be temperature controlled.

The continuous track of the present invention may adopt several configurations as outlined in, but not limited to, FIGS. 1A, 1B or 1C and 4A and 4B. In FIG. 1, the continuous track circumscribes the source. This configuration requires the use of cantilevered carriers extending from the rails so that the product, situated upon the carriers, extends outward over the source. This configuration results in greatly reduced attenuation and will be described in more detail below. However, it is to be understood that other embodiments of track configuration are considered within the scope of the present invention. For example, which is not to be considered limiting in any manner, in FIG. 4A, there is shown a multi-level, bar-bell shaped (in plan view) track that comprises two circular ends, one, or both of which (80, FIG. 4B) may be helical. In this configuration, the change in level of the track takes place at a helical end. However, the level-changing portion of track may also take place at other portions of the track, including linear sections of track.

The bar-bell-shaped track may be comprised of two horizontal positioned rails, spaced at a distance from each other and that span the source. In this configuration, the carrier is placed onto these rails. However, it is to be understood that other rail configurations of such a bar-bell shaped track are within the scope of the present invention, for example, a rail offset with respect to the source and engaged with a cantilevered carrier. The bar-bell track forms a continuous path from the load-unload area into the irradiation chamber and back. Within the irradiation chamber, the track is comprised of several levels that pass below and above the source in such a manner that the track lies directly above and below itself. A carrier placed on this track passes directly over or under the source, depending upon the level of track the carrier is on. The portion of track that passes by the source, when viewed in cross section, may be comprised of horizontally placed rails arranged one above another.

Other track configurations are also considered within the scope of the present invention providing that the change in the level of the track, from below to above the source, arises from the change in level of track, for example a helical portion of track or other level-changing portion of track.

By level-changing portion of track, it is meant the portion of track where the level of the track varies such that the track entering and exiting this portion of track does so at different levels. The level-changing portion of track may be positioned at a circular end of an elongated track, i.e. a helical portion of track, as shown in FIGS. 1A, 1B, 1C or 4B. However, the level-changing portion may also be placed within a section of track that is linear. Even though a continuous track is desired, slight variations in this design may exist without departing from the spirit and scope of this invention. For example, the level-changing portion of track may also be adjusted or engaged via the movement of a section of track via mechanical means. In this respect, the track of the present invention is continuous in nature, even though the level-changing section of track may be able to reversibly disengage with the track.

Below is described in more detail an embodiment of the present invention relating to the use of an elongated helical track as outlined in FIGS. 1A and 1B. In this embodiment, the track circumscribes the source, and cantilevered carriers, extending from the rails are used.

The continuous track, shown within the accompanying figures, comprise rails which are circular in cross section. However, it is considered within the scope of the present invention that the rail may be fashioned from an I-beam, C-beam, square tubing, or other such stock material as required. If a different rail material is used, then an appropriate wheel, that mates the rail will be required. The track of this invention may also comprise from one to a plurality of rails as needed. The present invention discloses a track comprising two rails (e.g. FIGS. 2, 4A, 4B and 5A), however, situations may arise where increased strength is required in order to support heavier product and a third, or more, rail(s) may be required for stability or support. Furthermore, the rails of the track are displayed within the accompanying figures as being located one above another. However, it is considered within the scope of the present invention that the rails may be offset with respect to each other (see for example FIG. 7, and corresponding carrier in FIG. 6). Such an offset may be preferred, for example but without wishing to limit the invention in any manner, to decrease the apparent length of cantilever of the carrier, or to aid in the addition of three or more rails to the track assembly.

Figure 5B:
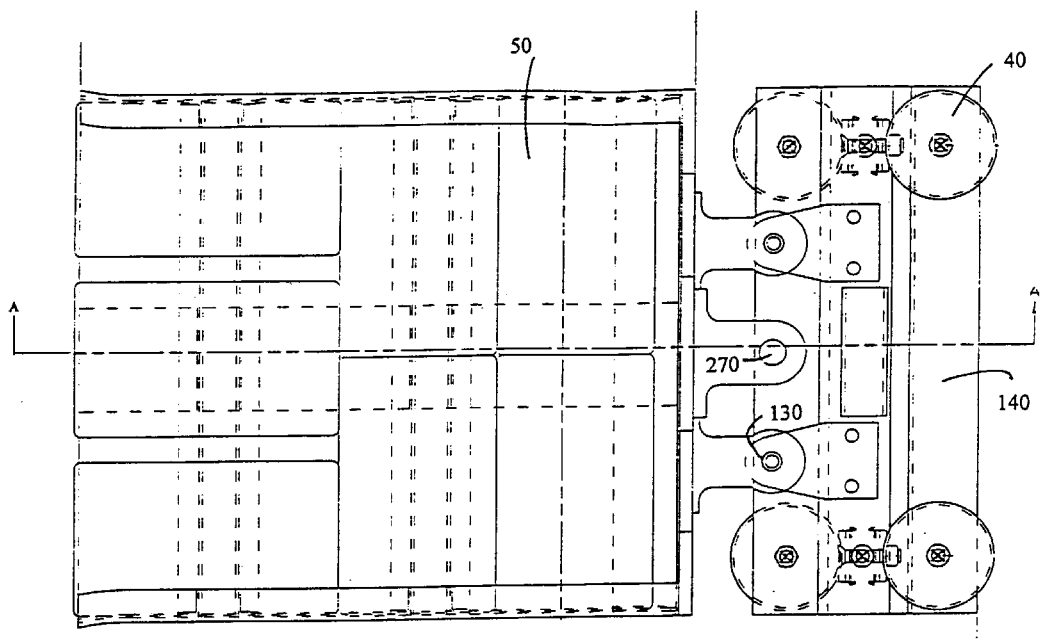
FIG. 5(B) shows a top view
Figure 5A:
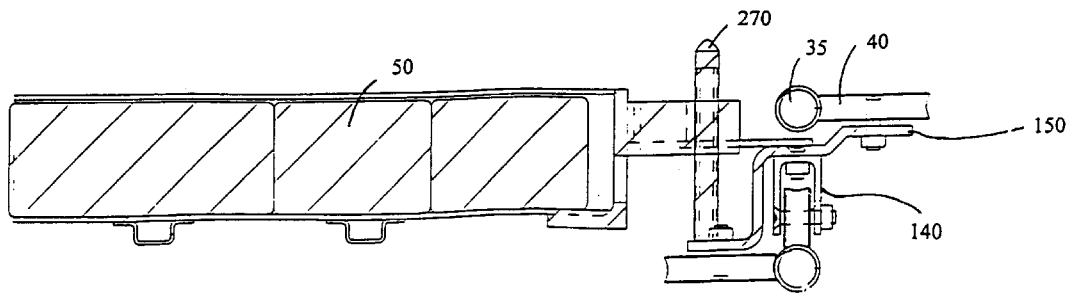
FIG. 5(A) shows a side view.
Figure 6:
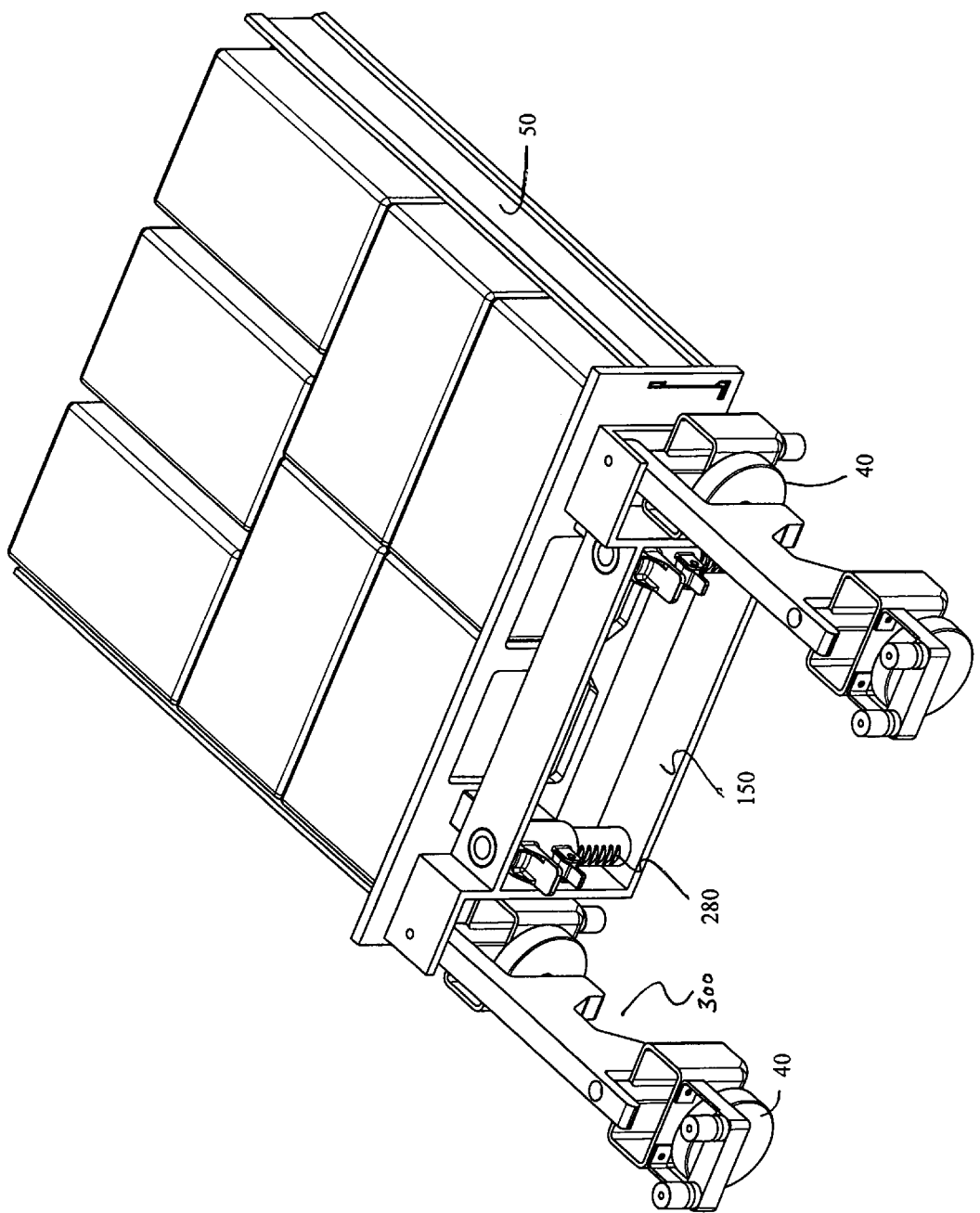
FIG. 6 shows, in perspective view, another aspect of an embodiment of the product irradiator of present invention of a carrier.
Figure 7:
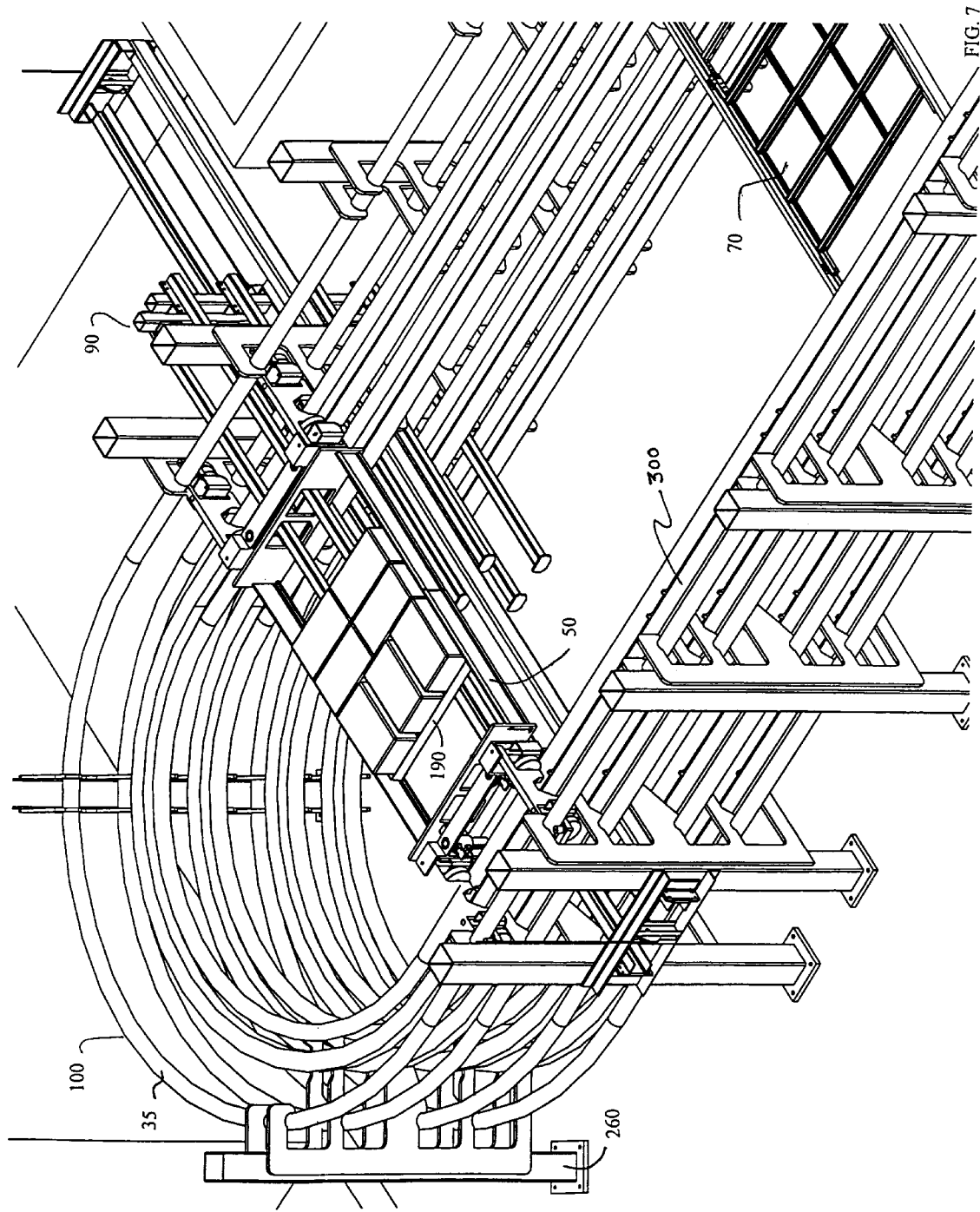
FIG. 7 shows, in perspective view, an aspect of an embodiment of the product irradiator of present invention and indicates the transfer of product from one carrier to another.

Carriers (50; FIGS. 5A, 5B and 6) are attached, typically along their side, to a wheel assembly (140) which comprises a frame (150), associated wheels (40), and a suitable attachment for attaching the wheel assembly to the tray. The carriers also comprise a suitable mechanism to interact with a drive mechanism (300, FIG. 7) capable of imparting movement onto the carrier. For example, which is not limiting in any manner, a dog or other suitable mechanism, for interacting with pins attached to a chain drive may be used as the drive mechanism. The chain drive would be typically aligned with the track and may be situated within an appropriate guide mechanism located between or near the rails in a spatial relationship that permits an interaction between the chain drive and carrier to take place.

Without wishing to limit the invention in any manner, the means of attachment between the wheel assembly and the carrier may comprise a series of pins (130), as indicated in FIG. 5A, or the wheel assembly may comprise pivoting arms that pivotally extend from the carrier and engage the rails via associated wheels (see FIG. 6). It is also considered within the scope of the present invention that a carrier may comprise steerable wheels that change orientation with respect to the carrier along different portions of the track. The carrier may comprise a lifting mechanism permitting a change in the height of the carrier with respect to the wheel assembly (270, FIGS. 5A and 5B; 280, FIG. 6). Along one edge of the carrier, there may also be placed a slow-speed drive engaging mechanism, such as a linear gear (rack) able to engage a drive pinion, if required. Such a slow speed drive may be used to regulate the speed of a carrier past the source.

Alternatives to a chain drive may be used in order to power the movement of the carrier along the continuous track. These may include methods known to one of skill in the art including mechanisms providing for a shuffle and dwell movement of the carrier using a power and free type of mechanism, so that the movement of the carrier may be indexed past the source. However, the carrier may also move in a continuous manner at a preset speed past the source. It is also contemplated that each carrier may be pushed along the track by a preceding carrier, or, that each carrier may comprise a separate drive motor. In these latter two embodiments, the carriers may not be associated with a drive chain. Such embodiments may permit easy maintenance of the drive motors or related moving parts associated with the drive mechanism as these components spend a considerable portion of time outside the irradiation chamber.

The wheel assembly may comprise four horizontal wheels as shown, for example in FIG. 5A, however, additional wheels may be used, or coupled and used in tandem as required in order to distribute the load accordingly. The wheel assembly (140) is engaged with the rails (35) and the carrier (50) in a manner that permits free movement of the carrier along the track and around the corners (i.e. circular ends of the elongated helical track, 80 and 100). The carrier (50), when engaged with the track, extends out from the track (30) and into the irradiation chamber (110). This design reduces attenuation of the radiation from the source. The outer side of the carrier, that is the side opposite from the side attached to the wheel assembly is open ended permitting sliding of the product off the carrier, should the need arise.

Figure 3:
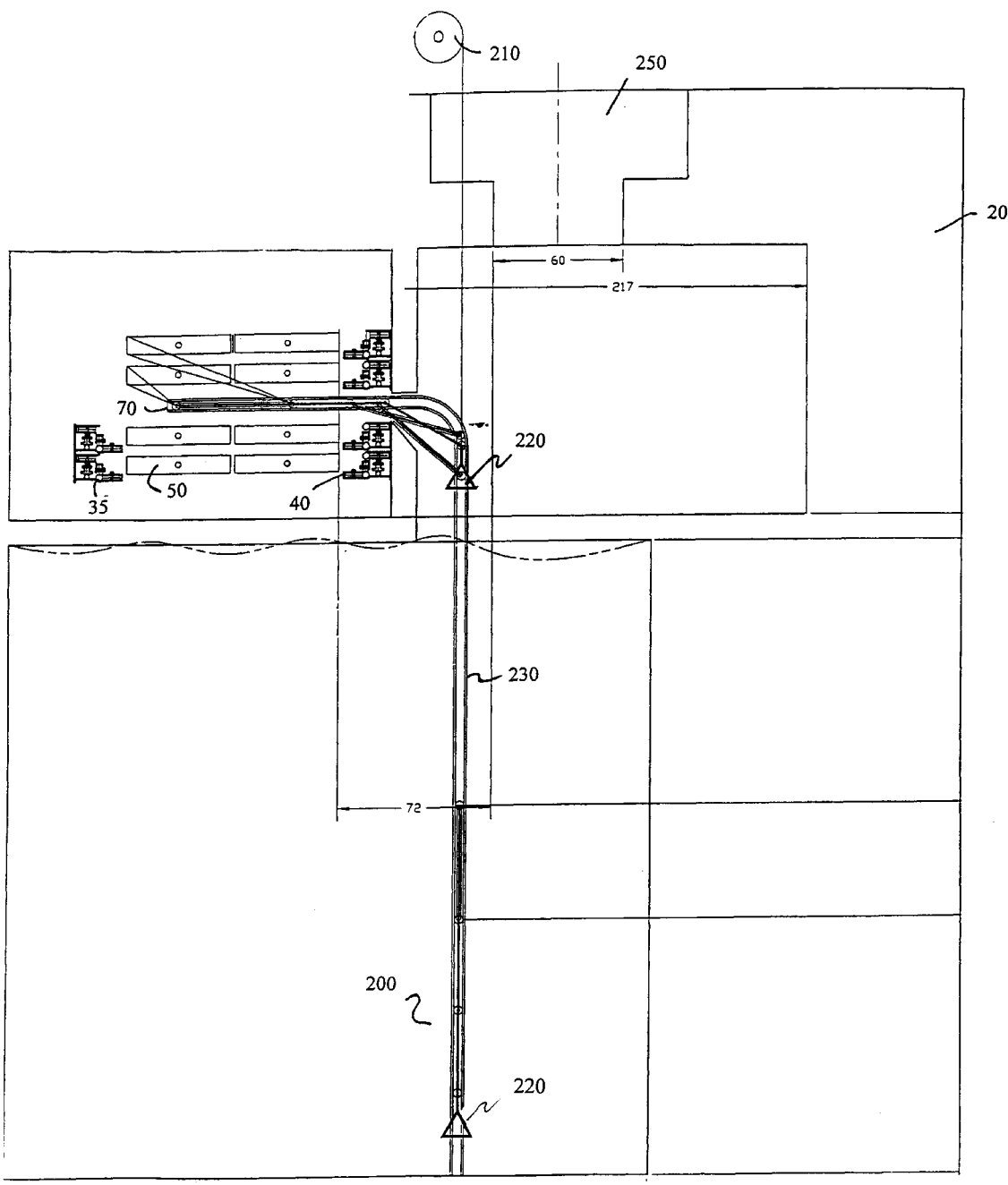
FIG. 3 shows in side view, an aspect of an embodiment of the product irradiator of present invention.

Somewhat centrally located within the irradiation chamber and within the perimeter of the track is a horizontally positioned source (70; see FIG. 2). The source is positioned in this manner in order to permit the travel of carriers both above and below the source (FIG. 3). This configuration permits irradiation of orientation-sensitive product within its native orientation. Furthermore, the horizontal attitude of the source, which is parallel to the carriers, ensures maximum exposure of the product to the source.

The source is stored within a pool (200) located below the building. The source is pulled up and into the irradiation chamber as required by a source rack hoist (210), and travels along a guide assembly (230) that directs the source rack into the irradiation chamber. The source rack is preferably counter weighted (220) so that return of the source rack into the subterranean pool takes place using gravity. Such an arrangement would permit the return of the source rack to the pool in the event of power loss. The guide assembly directs the source rack to adopt a horizontal position within the irradiation chamber. The position and size of the source rack within the irradiation chamber may be modified in order to permit typical product-source exposures. For example, either a source-overlapping-product (where the source extends beyond the perimeter of the product) or product-overlapping-source (where the product perimeter extends beyond the edge of the source) configuration may be used with the source rack-product arrangement of the present invention. It has been determined that a product-overlapping-source (POS) configuration generally results in a more efficient utilization of radiation provided by the source than a source-overlapping-product (SOP) configuration. Such a POS arrangement is displayed in FIG. 3, and is preferred. However, it is considered within the scope of the present invention that a SOP configuration may also be used within the present product irradiator under certain conditions. For example, an SOP configuration, wherein the source extends beyond the perimeter of the helical portion of the track, may be used if the product is not transferred from carrier to carrier as outlined below, but remains on a carrier throughout the carriers migration along the entire track. By adopting an SOP configuration complete and uniform exposure of the product to the source is ensured.

Any suitable source may be used within the source rack which produces gamma radiation, for example, but without limiting the invention any manner, cobalt 60 or cesium 137. The source is typically encapsulated and placed within a module comprising multiple capsules. The modules are placed within the source rack in a such a manner that a module and individual sources can be removed or relocated within the source rack as required.

The carrier is moved along the elongated helical path by any suitable drive mechanism, preferably one that permits the speed of the carrier to be varied should that need arise. For example, which is not to be considered limiting in any manner, one such drive mechanism is a chain drive comprising a plurality of pins which reversibly engage with each carrier via dogs pivotally attached to the carrier. In this embodiment, the dogs are attached to the front of a carrier and they are biased outwards from the carrier, towards the chain drive thereby ensuring contact with a pin. Once contact between the dog and pin is made, the carrier is moved along the track by the chain drive. When a carrier is to stop, the dog disengages from the pin attached to the drive chain. This disengagement may be accomplished through the use of stop links attached to the back of a preceding carrier which are capable of disengaging a dog attached to the front of an upcoming carrier, releasing the dog from the pin of the drive chain. Otherwise, the dogs may be disengaged at desired positions around the track by any suitable positioned mechanism that releases a dog from a pin. This arrangement permits the carriers within the irradiation chamber to shuffle and dwell as required, in order to optimize the exposure of the product to the source. Other alternatives to the chain drive may be used in order to power the movement of the carrier along the continuous track. These methods include any suitable power and free mechanism to move the carrier as desired, pushing the carrier along the track by a preceding carrier, or, it is also contemplated that each carrier may comprise its own drive motor, pneumatic hydraulic cyclinders, or push/pull cable mechanisms.

The rails form an essentially elongated helical path around a centrally located radiation source (70) so that the carriers pass both below and above the source. The passing of a carrier both above and below the source is accomplished by changing the level of the track relative to the source. This change in track level may occur at one end of the elongated helical assembly (see FIG. 1C), as generally indicted as 80 (FIG. 1A), at both circular ends of the track (FIG. 4), or along a linear portion of track. With the design of this embodiment of the present invention, the product and carrier pass the source (70) at a predetermined distance in both the vertical and horizontal dimension. Following one revolution around the track, the carrier changes its level relative to the source as dictated by the track. This arrangement provides for the sequential exposure of both the top and bottom areas of the product to the source, and ensures that the product receives a uniform exposure to the source through a variety of exposure intensities.

As indicated above, other track configurations may be employed in order to achieve the sequential exposure of the product at different levels to the source, providing that the change in carrier level, with respect to the source, arises due to a change in the level of continuous track. Such configurations include, but are not limited to the bar-bell shaped track as described previously, where the portion of track that traverses the source is aligned one on top of another. In this embodiment, the horizontal carrier is positioned over two horizontal rails that are spaced apart so that they approximately span the source. It is also contemplated, and considered within the scope of the present invention, that a similar, bar-bell shaped track design may involve the use of cantilevered carriers extending from a track assembly that is offset with respect to the source.

The uniform exposure of the product to the source results in an optimal DUR (dose uniformity ratio). The number of passes of the product by the source is dependant upon the type of product being irradiated. For example, low density products do not absorb as much radiation as a higher density product for a given depth of penetration, and therefore require more exposure to the source for a specified minimum dose. This can be accomplished by either permitting the product to dwell for longer periods of time near the source (i.e. disengage the carrier from the drive mechanism), or by slowing the drive mechanism. The number of passes within the irradiation chamber may be increased by adding more levels to the track in order to increase utilization efficiency of the source. The number of levels of track within the irradiation chamber may be selected based upon consideration of the efficiency of source utilization desired, balanced with the amount of time associated with product hold-up within the irradiator.

The present invention also permits for the re-orientation of the product upon the carrier. Such a product re-orientation may be obtained by rotating the product on a carrier via a suitable mechanism so that the side of the carrier originally facing the source is now rotated 180° and faces away from the source. This re-orientation may also be accomplished by the transfer of product from a first to a second carrier using a pusher (90; see FIG. 7). This transfer process is generally indicated as 90 in FIGS. 1A and 1B. The re-orientation of product upon the carrier ensures a more uniform dose of the product when the POS (product-overlapping-source) configuration is used within the irradiation chamber. However, it is to be understood that if the SOP configuration is used with the product irradiator of the present invention, then there may be no need to re-orient the product, or adopt the use of the pusher nor any need to transfer product from one carrier to another. This is because with the SOP configuration, the source extends beyond the permitter of the product, and all areas of the product are exposed to the source. However, as indicated above, this configuration (SOP) is less efficient that the POS configuration, but may be used in some circumstances in order to simplify the process and reduce product hold-up.

By following the elongated helical track of the present invention the product-loaded carriers travel either above or below the radiation source in a first direction. At the end of this exposure path, and before a first helical end-portion of the track, generally indicated as 100 (FIGS. 1A and 1C), the product may be transferred from its carrier onto a second carrier which is engaged with an opposing track. This transfer, and migration of the carrier from the first helical end (100) to the second helical end (80) of the track permits exposure of the opposite side of the product to the source in a second direction. In this embodiment, the carriers traverse the first helical end-portion of the track (100) free of product. At the first end of the elongated helical track (100), the track remains at the same level as either the approach or receding track, and no change in elevation occurs. At the second end of the elongated helical path, generally indicated as, 80 (FIG. 1C), the track changes elevation permitting a carrier migrating along this portion of the track to alter its distance from the source in the vertical dimension. However, as indicated above, the change in level of the track may take place at other portions of the track aside from the second end, including linear portions of track.

The product can be pushed from a first to second tray (as generally indicated by 90 in FIG. 7) using a pusher mechanism so that products at different levels of the track can all be pushed at the same time via the single mechanism. As an example, which is not to be considered limiting in any manner, product may be placed upon slave trays (190) positioned within the carrier, and the movement of the slave tray from carrier to carrier will result in the transfer of product from a first to second carrier (see for example FIG. 7). The pusher driving mechanism is not shown in FIG. 7 for clarity, however, it may be housed overhead on the rooftop in order to reduce the number of moving parts within the irradiation chamber.

Each tray has an optional height adjustment (e.g. 270 or 280, in FIGS. 5A and 5B or 6, respectively) in order to permit adjustment of each carrier in order to accommodate products of varying height, and in order to optimize the DUR while maintaining maximum product throughput. Without wishing to limit the invention in any manner, such height adjustments may include a screw-adjust mechanism as portrayed in 270 FIG. 5A, ratchet mechanism (280, see FIG. 6), a ramp assembly, or any other suitable means. It is contemplated that the height adjustment may be made while the carrier is travelling around the track in order to permit continuous exposure of product and minimize down time. By providing for the change in height of the carrier with respect to the wheel assembly, the carrier may easily accept products of varying dimensions should the need arise. It is also possible to achieve the same effect of carrier height adjustment by increasing the separation between the levels of track. In this regard, the supports, 260, may comprise a height adjust mechanism.

A problem with prior art irradiators, is that the carriers can not easily accommodate variations in product size since the carriers used are of a fixed dimension, and the track, or conveyor, assemblies are fixed at preset distances from the source. Typically, the DUR for a product is specified and the packing of product within the carrier is altered to achieve the required DUR. For some products it is necessary to pack them centrally within the carrier, and fill the surrounding space with a filler material. This results in low packing efficiencies within the carrier and reduced product throughput, however, it also results in low utilization efficiency of the source.

It is considered within the scope of the present invention that the principle associated with adjustable carrier height (as described above) may also be applied to product irradiators using a vertical source type arrangement as typically found in the prior art (e.g. U.S. Pat. Nos. 5,396,074, 5,001,352, 4,866,281, 4,852,138, 4,561,358, 4,481,652, 3,676,675 or 3,564,241). However, in this embodiment, since the source is vertical, the carriers are typically taller than wide, and in order to optimize product throughput, and remain within the specified DURs the width of prior art carriers would need to be varied. The change in width of such carriers could be accomplished in a variety of ways including carriers capable of adjusting their width, or using an appropriately sized carrier. To further optimize carrier spacing, the wheel assemblies may be adjustable in an analogous manner as described above for a horizontal carrier to accommodate variable carrier widths. Furthermore, the track or conveyor assemblies may need to be spaced apart from one another in order to allow oversize (wider) carriers to pass side-by-side before the source. Therefore, the spacing of the track or conveyor assemblies may also be adjustable.

It is preferred that the track or conveyor passed by the source at least two levels in order to increase the efficiency of source utilization. The adjustment in the level change of the track or conveyor may take place using any prior art mechanism, or an analogous system as that disclosed in the present invention wherein the track, or conveyor, includes a level-changing portion. However, single pass irradiators may also benefit from the use of an adjustable carrier.

The design of the carrier of the present invention provides for at least one adjustable carrier dimension. In the case of a horizontal source and carrier, the carriers are ajdustable to provide variable height, and in the case of a vertical source and carrier, the carriers are adjusted to provide a variable width. The variability in carrier dimension permits the efficient loading of a wide range of product sizes, ensures that the specified DUR is achieved, and optimizes product throughput.

Without wishing to limit the invention in any manner, the following examples are provided.

EXAMPLE 1

Product Densities of 0.4–0.9 g/cc

Based on the relationship between a product and source, using the product irradiator of the present invention, the efficiency of radiation utilization with varied product density and product configuration can be determined. The following assumptions have been made for the following calculations. It is to be understood that each of these assumptions is not to be considered limiting in any manner:

the radiation source is cobalt 60;

the product is a red meat such a hamburger, with several packaged-product heights of 6, 9, or 12 inches (industry standards for such a product are between 6 to 11 inches). However, it is to be understood that products with a similar density range and with a greater height, up to about 16 inches, may also be used in accordance with the present invention. Similarly, medical materials, which are of a lower density may be up to about 32 inches in height, and can be treated using the irradiator of the present invention;

the product passes the source 4 times (4-pass), that is the product passes the source two times below the source, completing two revolutions around the helical track, and then passes the source two times above the source, completing two more revolutions around the track, for a total of four revolutions of the track around the source. However, it is to be understood that from 2 to 8 passes may be used with the product irradiator of the present invention.;

the configuration is product-overlapping-source.

Figure 8:
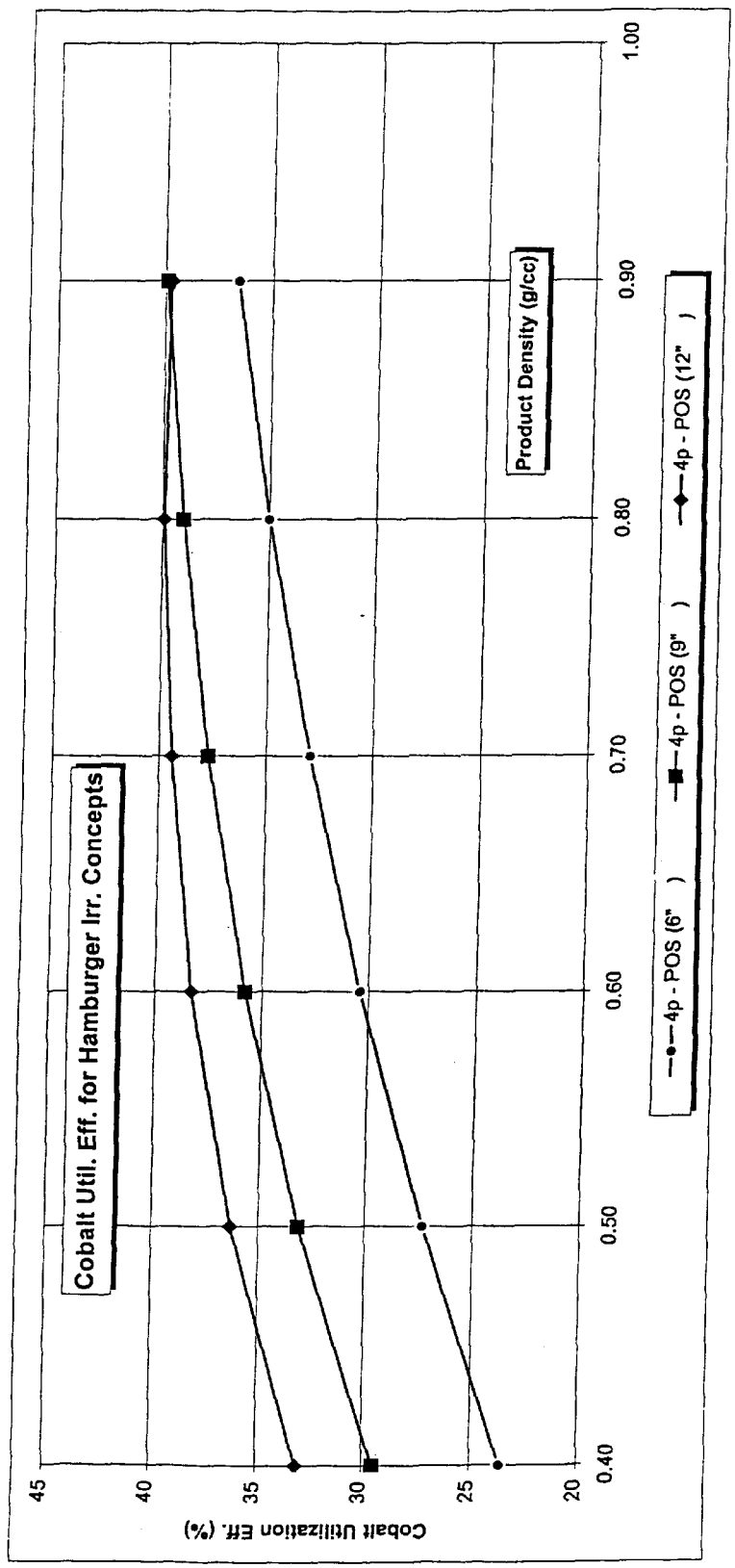
FIG. 8 shows the efficiency of utilization of a radiation source, in this case cobalt 60 by a product, in this case red meat (hamburger), over various product densities and three different product heights of 6, 9 and 12 inches. For this determination, the product passes the source 4 times in diameter directions (4p), that is, the product makes four revolutions around the helical track before exiting the irradiation chamber. Furthermore, the product-source configuration is product-overlapping-source (POS).

Other assumptions include set distances between the product and source on each pass, a uniform density of the product, 5 carriers per pass placed on the track, and a predefined amount of aluminum surrounding the product from the carrier or slave tray. The results of such a set of calculations, directed at determining the efficiency of radiation utilization are presented in FIG. 8. The results demonstrate that radiation efficiencies for a 4-pass exposure of product reach upward of 40%. As indicated above, products of lower densities will result in lower efficiencies of source utilization.

Figure 9:
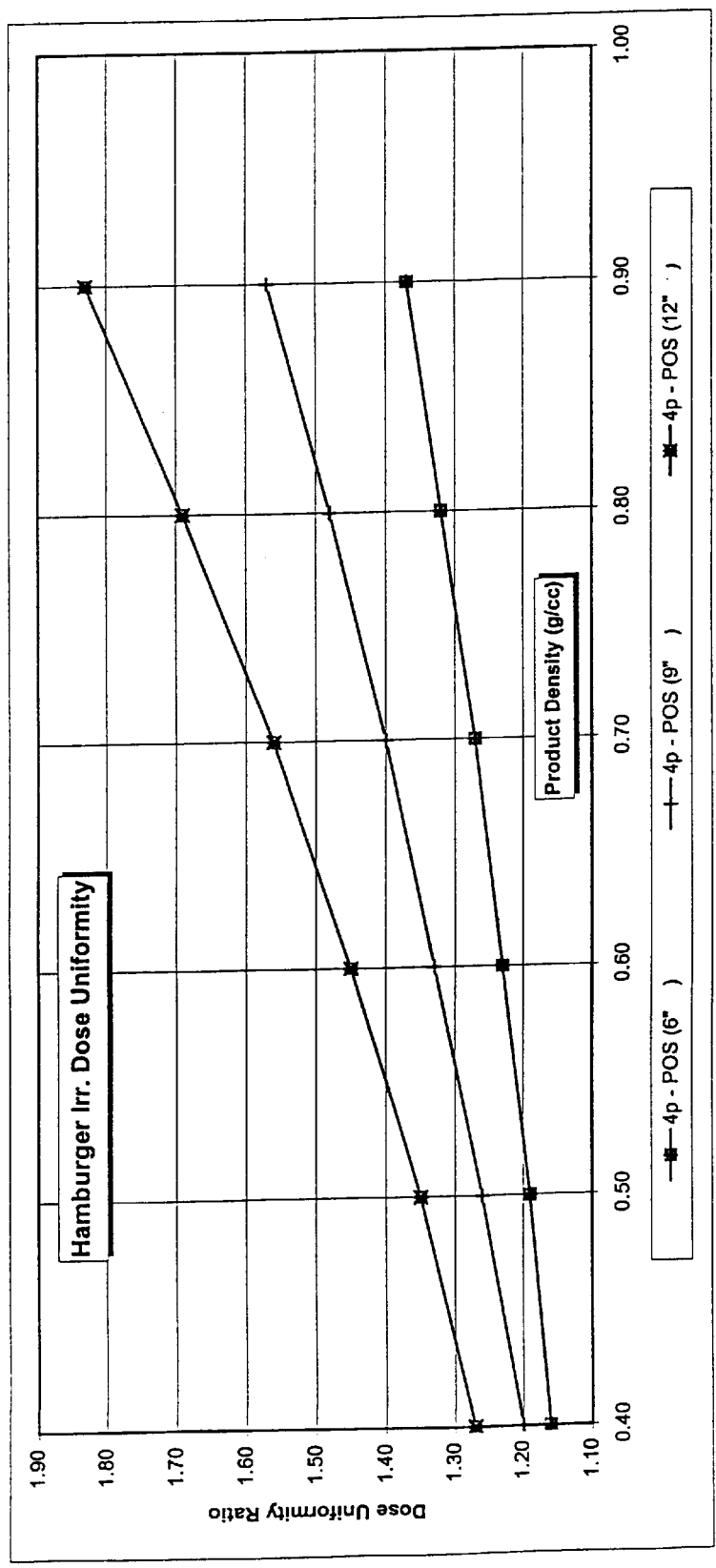
FIG. 9 shows the dose-uniformity ratio (DUR) of a product, in this case red meat (hamburger), over various product densities, and three different product heights of 6, 9 and 12 inches. For this determination, the product passes the source 4 times in both directions (4p), that is, the product makes four revolutions around the helical track before exiting the irradiation chamber. Furthermore, the product-source configuration is product-overlapping-source (POS).

A similar set of calculations, incorporating the same assumptions as outlined above may be used to determine the dose-uniformity-ratio (DUR) for several product conformations. In general, the DUR indicates the range of absorbed dose a product has received. With products of greater dimension (especially height, with respect to the source), a larger value for DUR will be obtained since the outer regions of the product will be exposed to a greater amount of irradiation than the inner regions of the product. The difference between the does received throughout the product arising from exposure to the radiation source is reflected in the DUR. DURs of up to about 1.5 are considered acceptable within the art of red-meat irradiation. As can be seen from FIG. 9, acceptable DURs are obtained using product configurations that span a range of product densities, and dimensions including 6, 9 or 12 inches in height. These product configurations span the industry standards for such product packages (i.e. 6–11 inches), indicating that no-repackaging of product is required from industry standard products to packaging which is suitable for irradiation using the product irradiator of the present invention. Prior art irradiators, for example electron beam irradiators, are limit to product conformations with a reduced height since they exhibit poor depth penetration at product densities above 0.4 g/cc. The use of such irradiators for product treatment necessitates re-packaging the product prior to irradiation (and re-packaging prior to delivery of treated product). For example, using electron beam irradiation, optimal DUR levels are obtained with products of only 4 inches in height for a product with a similar density, therefore extensive handling and repackaging of product is required. With the product irradiator design of the present invention, optimal DURs are obtained with products ranging from about 6 to about 12 inches in height, and over a range of product densities, thereby requiring no product repackaging prior to treatment. However, it is to be understood that products with a similar density range and with a greater height, up to about 16 inches, may also be used in accordance with the present invention and still obtain optical DUR levels. Furthermore, disposable medical materials, which are of a lower density than that described above, may be up to about 36 inches in height, and can be treated using the irradiator of the present invention.

The fact that a broad range of packaging dimensions, over a set range of product density, results in similar DURs, ensures that minimal or no product repackaging is required during both loading, or unloading and re-palleting product, when treated using the product irradiator of the present invention.

Based on the above assumptions it has also been determined that for 100 kCi of cobalt-60, and 1.5 kGy Dmin, from about 0.8 to about 1.4 tonnes of product can be processed per hour over a range of product densities from about 0.4 to about 0.9 g/cc. For 1 MCi cobalt-60 and a Dmin of 1.75 kGy, from about 6.9 tonnes/h, to about 12 tonnes/h can be processed over a density range from about 0.4 g/cc to about 0.9 g/cc, respectively. Using the irradiator of the present invention up to 200 million pounds of product, such as red meat can be processed per year.

EXAMPLE 2

Product Densities up to 0.3 g/cc

As outlined in Example 1, the following assumptions have been made for the following calculations. It is to be understood that each of these assumptions is not to be considered limiting in any manner:

the radiation source is cobalt 60;
the product is a low density product such as a medical disposable item, with a packaged-product height of one meter (approx 36 inches);
the product passes the source 4 times (4-pass), that is the product passes the source two times below the source, completing two revolutions around the helical track, and then passes the source two times above the source, completing two more revolutions around the track, for a total of four revolutions of the track around the source. However, it is to be understood that from 2 to 8 passes may be used with the product irradiator of the present invention.;
the configuration is product-overlapping-source.

Figure 10:
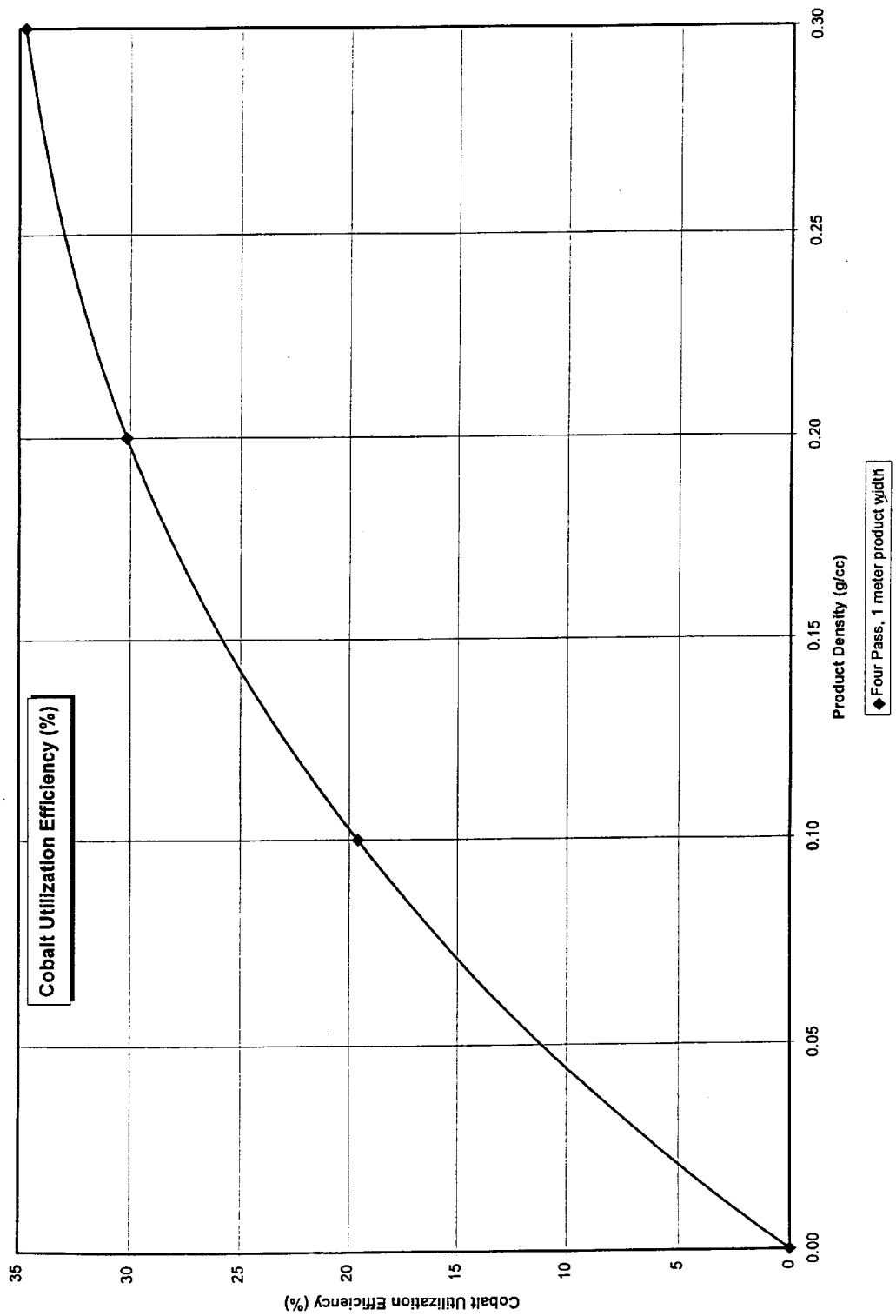
FIG. 10 shows the efficiency of utilization of a radiation source, in this case cobalt 60 by a product, in this case medical devices, over various product densities. For this determination, the product passes the source 4 times in both directions (4p), that is, the product makes four revolutions around the helical track before exiting the irradiation chamber. Furthermore, the product-source configuration is product-overlapping-source (POS).

Other assumptions include set distances between the product and source on each pass, a uniform density of the product, 5 carriers per pass placed on the track, and a predefined amount of aluminum surrounding the product from the carrier or slave tray. The results of such a set of calculations, directed at determining the efficiency of radiation utilization are presented in FIG. 10. The results demonstrate that radiation efficiencies for a 4-pass exposure of product reach upward of 35%. As indicated above, products of lower densities will result in lower efficiencies of source utilization.

Figure 11:
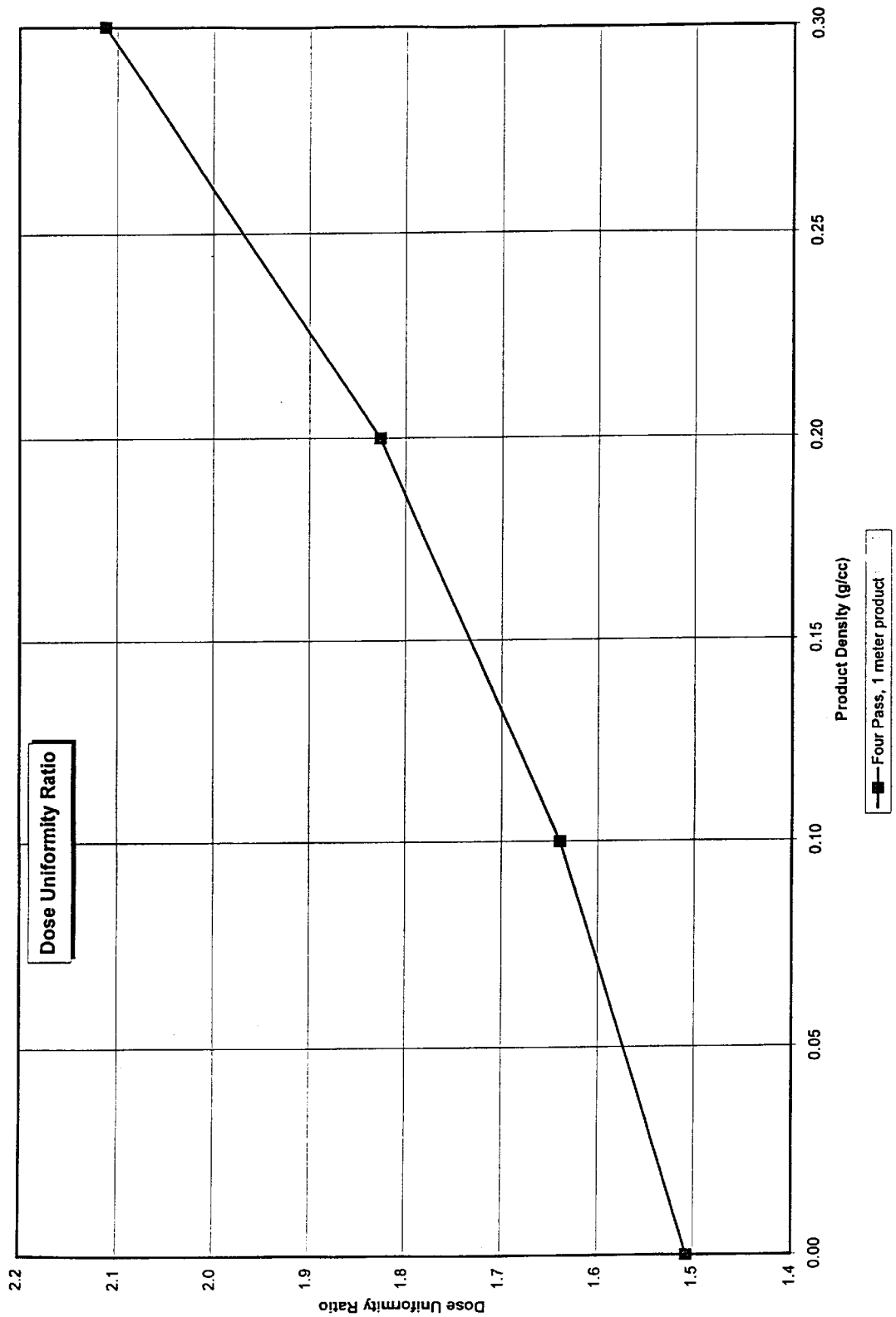
FIG. 11 shows the dose-uniformity ratio (DUR) of a product, in this case medical devices over various product densities. For this determination, the product passes the source 4 times in both directions (4p), that is, the product makes four revolutions around the helical track before exiting the irradiation chamber. Furthermore, the product-source configuration is product-overlapping-source (POS).

A similar set of calculations, combined with a 1M product height and incorporating the same assumptions as outlined above were used to determine the dose-uniformity-ratio (DUR) for several product densities. As can be seen from FIG. 11, DURs of from 1.5 to about 2.1 are obtained. Again this incidates that no-repackaging of product is required from industry standard products to packaging which is suitable for irradiation using the product irradiator of the present invention.

Based on 1MCi Cobalt-60 and 25 kGy Dmin, the irradiator of the present invention can process from about 700,000 cubic feet to about 1.1 million cubic feet over a range of product densities from about 0.1 to about 0.3.

All documents referred to herein are incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A product irradiator comprising:
   i) a loading-unloading area and an irradiation chamber;
   ii) a continuous, substantially elongated helical track having a level-changing portion, said continuous track entering and exiting said irradiation chamber from said loading-unloading area, said continuous track comprised of at least one rail and of at least two levels;
   iii) a radiation source located within said irradiation chamber;
   iv) a substantially horizontal carrier engaged to said at least one rail; and
   v) at least one drive mechanism capable of moving said carrier along said continuous track.

2. The product irradiator of claim 1, wherein said radiation source is either cobalt 60 or cesium 137.

3. The product irradiator of claim 2, wherein said continuous track comprises up to eight levels within said irradiation chamber.

4. The product irradiator of claim 3, wherein said continuous track is bar-bell shaped track.

5. The product irradiator of claim 3, wherein said radiation source is centrally positioned within said elongated helical track.

6. The product irradiator of claim 5, wherein said source lies in a substantially horizontal rack within said irradiation chamber.

7. The product irradiator of claim 5, wherein said elongated helical track comprises either two, four six or eight levels.

8. The product irradiator of claim 7, wherein said radiation source is positioned with an equivalent number of said levels of elongated helical track lying above said radiation source, as levels of elongated helical track that lie below said radiation source.

9. The product irradiator of claim 8, further comprising a product re-orienting mechanism.

10. The product irradiator of claim 9, wherein said radiation source adopts a product-overlapping-source configuration.

11. The product irradiator of claim 10, wherein said substantially horizontal carrier is engaged to said at least one rail by a wheel assembly, said wheel assembly is pivotally attached along one side of each of said horizontal carrier.

12. The product irradiator of claim 1, wherein said continuous track is comprised of two rails.

13. The product irradiator of claim 12, wherein said rails are offset with respect to each other.

14. The product irradiator of claim 1, wherein said radiation source is comprised of source modules.

15. The product irradiator of claim 14, wherein said radiation source is stored below the irradiation chamber.

16. The product irradiator of claim 14, wherein said radiation source is brought into a substantially horizontal position within said irradiation chamber using a source rack hoist and guide assembly.

17. The product irradiator of claim 1, wherein said irradiation chamber is temperature controlled and ranges from about −25° C. to about 25° C.

18. The product irradiator of claim 1, wherein said irradiation chamber is located within a building comprising concrete, lead, or both concrete and lead, walls and roof.

19. The product irradiator of claim 18, wherein said roof further comprises a multipiece roof plug, permitting access to said irradiation chamber.

20. The product irradiator of claim 19, further comprising a maze located between said loading-unloading area and irradiation chamber, said continuous track travelling through said maze.

21. The product irradiator of claim 1, wherein said carrier travels along said continuous track at different speeds.

22. The product irradiator of claim 1, wherein at least one, of said at least one drive mechanism, comprises a chain drive with a plurality of outwardly extending pins, each of said plurality of outwardly extending pins capable of engaging with a dog attached to said carrier and pivotally biased in the direction of the chain drive, so that when said dog is engaged with one of said plurality of outwardly extending pins, said carrier is moved along said continuous track by said chain drive.

23. The product irradiator of claim 22, further comprising a stop link capable of disengaging said dog from one of said outwardly extending pins, thereby permitting said carrier to stop along said continuous track.

24. The product irradiator of claim 23, wherein said stop link is attached to the rear of said carrier, and said dog is attached to the front of said carrier, so that when two carriers abut each other, said dog disengages with said drive chain.

25. The product irradiator of claim 1, wherein the height of said carrier, with respect to said continuous track, can be altered by a height adjust mechanism.

26. The product irradiator of claim 25, wherein the height adjust mechanism is a screw mechanism, a ramp mechanism, a piston-driven mechanism, a ratchet mechanism, or a combination thereof.

27. The product irradiator of claim 1, characterized with a dose-uniformity-ratio of up to about 2.2 for a product having a density of about 0.01 to about 0.9 g/cc, and said product between from about 6 to 36 inches in height.

28. A product irradiator comprising:
   i) a temperature controlled building, within which is located a loading-unloading area, a maze, an irradiation chamber, and a radiation source storage area, said building comprised of concrete, lead, or both concrete and lead, wherein the temperature of said loading-unloading area, maze, and irradiation chamber is from about −25° C. to about 25° C.; said building further comprising a multipiece roof plug permitting access to said irradiation chamber and radiation source storage area;
   ii) a continuous track extending from said loading-unloading area through said maze and into said irradiation chamber, said continuous track having a level-changing portion, and comprised of at least one rail, said continuous track comprising either two, four, six or eight levels, said continuous track having an elongated helical portion;
   iii) at least two carriers, each carrier comprising a slave tray and a wheel assembly, said wheel assembly engaged with said at least one rail and pivotally attached along one side of each carrier, each carrier extending substantially horizontally from said continuous track toward said radiation source;
   iv) at least one drive mechanism capable of moving each of said at least two carriers along said continuous track from said loading-unloading area, through said maze, into said irradiation chamber, and travelling over said level-changing portion of track, thereby changing horizontal and vertical position of said carrier with respect to said radiation source within said irradiation chamber, exiting said irradiation chamber, and travelling through said maze to said loading-unloading area;
   v) a pusher capable of transferring a product located upon said slave tray from a first carrier to a second carrier;
   vi) an radiation source stored below said irradiation chamber within said source storage area, said source brought into a substantially horizontal position within said irradiation chamber using a source rack hoist and guide assembly, when positioned within said irradiation chamber said radiation source is located centrally, on a horizontal plane, within said elongated helical portion of said continuous track, and positioned with an equivalent number of levels of track lying above said radiation source, as levels of continuous track that lie below said radiation source; said radiation source adopting a product-overlapping-source configuration with respect to said product, said radiation source selected from either cobalt 60 and cesium 137.

29. The product irradiator of claim 9, further comprising at least two carriers, wherein said product re-orienting mechanism comprises a pusher capable of transferring said product from a first carrier to a second carrier.

30. The product irradiator of claim 1, wherein said carrier is insulated.

31. A product irradiator comprising; a loading-unloading area and an irradiation chamber; a conveying means; a radiation source located within said irradiation chamber; a carrier; and, at least one drive mechanism capable of moving said carrier along said conveying means, wherein at least one dimension of said carrier is variable.

32. The product irradiator of claim 32, wherein said carrier comprises a wheel assembly that is adjustable in said at least one dimension.

33. The product irradiator of claim 31 wherein said source is oriented horizontally within said irradiation chamber, and said at least one dimension is the height.

34. The product irradiator of claim 31 wherein said source is oriented vertically within said irradiation chamber, and said at least one dimension is the width.

35. The product irradiator of claim 31 wherein said conveying means is selected from an overhead track, a under-carrier track, or a combination thereof.

36. The product irradiator of claim 31 wherein said conveying means comprises more than one level.

37. The product irradiator of claim 36 wherein said conveying means includes a level-changing portion.

38. A product irradiator comprising:
   i) a loading-unloading area and an irradiation chamber;
   ii) a continuous elongated helical track having a level-changing portion, said continuous track entering and exiting said irradiation chamber from said loading-unloading area, said continuous track comprised of at least one rail and of at least two levels;
   iii) a radiation source located within said irradiation chamber;
   iv) a substantially horizontal, cantilevered, carrier engaged to said at least one rail; and
   v) at least one drive mechanism capable of moving said carrier along said continuous track.

39. A product irradiator comprising:
   i) a loading-unloading area and an irradiation chamber;
   ii) a continuous elongated helical track having a level-changing portion, said continuous track entering and exiting said irradiation chamber from said loading-unloading area, said continuous track comprised of at least one rail and of at least two levels within said irradiation chamber, said track oriented towards the perimeter of said irradiation chamber;

iii) a radiation source located within said irradiation chamber;
iv) a substantially horizontal, cantilevered, carrier engaged to said at least one rail; and
v) at least one drive mechanism capable of moving said carrier along said continuous track.

* * * * *